United States Patent [19]

Strong et al.

[11] 4,004,023

[45] Jan. 18, 1977

[54] 1-(4-BUTYLPHENYL)-1-(3,4-METHYLENEDIOXYPHENYL)-2-NITROALKANES AND SYNERGISTIC INSECTICIDAL MIXTURES THEREWITH

[75] Inventors: Jerry Glenn Strong, Warren; Harold Alexander Kaufman, Piscataway, both of N.J.

[73] Assignee: Mobil Oil Corporation, New York, N.Y.

[22] Filed: Oct. 1, 1975

[21] Appl. No.: 618,660

[52] U.S. Cl. .......................... 424/282; 260/340.5; 260/612 R; 260/618 B
[51] Int. Cl.² .................................. C07D 317/44
[58] Field of Search ............... 260/340.5; 424/282

[56] References Cited

UNITED STATES PATENTS

| 3,823,192 | 7/1974 | Holan et al. | 260/340.5 X |
| 3,884,938 | 5/1975 | Holan | 260/340.5 |

*Primary Examiner* — Ethel G. Love
*Attorney, Agent, or Firm* — Charles A. Huggett; Hastings S. Trigg

[57] ABSTRACT

1-(4 Butylphenyl)-1-(3,4-methylenedioxyphenyl)-2-nitroalkanes are novel compounds, possessing a broad range of insecticidal effectiveness, which when admixed with 1-(p-alkylphenyl)-1-(p-alkoxyphenyl)-2-nitroalkanes provide synergistic insecticidal compositions effective at low concentrations.

9 Claims, No Drawings

1-(4-BUTYLPHENYL)-1-(3,4-METHYLENEDIOXY-PHENYL)-2-NITROALKANES AND SYNERGISTIC INSECTICIDAL MIXTURES THEREWITH

CROSS-REFERENCE TO RELATED APPLICATION

Ser. No. 410,935 filed Oct. 20, 1973 entitled 1,1-DIPHENYL-2-NITROALKANES now pending.

BACKGROUND OF THE INVENTION

1. Field of the Invention

This invention is directed towards novel 1-(4-butylphenyl)-1-(3,4-methylenedioxyphenyl-2-nitroalkanes, e.g., nitropropanes and butanes. These compounds are effective in combatting various insect species including such public health pests as housefly and mosquito and the major beetle and worm pests of agriculture, e.g., Mexican bean beetle and Southern armyworm.

This invention is also directed towards a highly effective synergistic combination of these new compounds and other 1,1-diphenyl-2-nitroalkanes, e.g., 1-(p-alkylphenyl)-1-(p-alkoxyphenyl)-2-nitroalkanes such as 1-(p-tertiary-butylphenyl)-1-(p-ethoxyphenyl)-2-nitrobutane.

2. Description of the Prior Art

The prior art, (e.g., German Patent Publication No. DT-2404914 and preliminary Swiss application No. 5-8631) discloses 1-(4-alkylphenyl)-1-(3,4-methylenedioxyphenyl)-2-nitroalkanes wherein the alkyl group is $C_1$–$C_3$ alkyl. Also disclosed therein are combinations of such compounds with each other and with other insecticidal compounds.

With respect to the 1-(p-alkylphenyl)-1-(p-alkoxyphenyl)-2-nitroalkanes the prior art (e.g., preliminary Swiss application No. 5-8631) discloses 1,1-diphenyl-2-nitropropane or butane derivatives of the following structure:

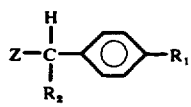

where $R_1$ is $C_{1-3}$ alkyl, $R_2$ is interalia p-$C_{1-3}$-alkoxyphenyl and Z is $NO_2$—CH—$CH_3$ or $NO_2$—CH—$C_2H_5$ as being useful insect control agents.

Additionally, DDT-like compounds, for example methyl methoxychlor and methyl ethoxychlor, are known to be effective insecticides; see for example, I. P. Kapoor et al., J. Ag. Food Chem., 18, 1145 (1970) and R. L. Metcalf et al., Bull Wld. Hlth. Org., 44, 363 1971. U.S. Pat. No. 2,716,627 discloses 1-aryl derivatives of 2-nitro-1-p-isopropylphenylalkanes as being suitable for use as insecticides.

The hereindisclosed and claimed compounds, i.e. 1-(4-butylphenyl)-1-(3,4-methylenedioxyphenyl)-2-nitroalkanes are a new class of insecticides possessing a broad spectrum of effectiveness. Further, in view of any art known to applicants', combinations of these new compounds with 1-(p-alkylphenyl)-1-(p-alkoxyphenyl)-2-nitroalkanes, e.g., 1-(p-tertiary butylphenyl)-1-(p-ethoxyphenyl-2-nitrobutane possess at low application rates surprising and unobvious synergistic insecticidal properties. Compositions of these two compound types are widely insecticidally effective at application rates of even less than 100 ppm or 0.01%, i.e., by weight of the insect-control agent in the composition thereof with a carrier.

SUMMARY OF THE INVENTION

This invention is more particularly directed to a novel class of compounds having broad effectiveness as insect-control agents or insecticides, mixtures thereof and compositions comprising the compounds and an inert solid or liquid carrier therefor.

The compounds within the scope of this invention have the following general structure:

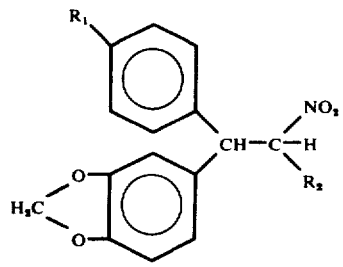

wherein $R_1$ is $C_4$ alkyl, branched or unbranched and $R_2$ is methyl or ethyl, i.e., $CH_3$ or $C_2H_5$. $R_1$ is more specifically selected from the butyl group consisting of normal-butyl, secondary-butyl, isobutyl and tertiary-butyl. Preferred embodiments include such compounds where $R_1$ is tertiary-butyl.

This invention further relates to the use of these compounds as insect-control agents in combatting insects and to insecticidally effective compositions of matter comprising at least one such compound or mixture thereof and/or an inert solid or liquid carrier therefor.

Additionally, this invention relates to the use of these compounds in combination with other insecticides, e.g., 1-(p-alkylphenyl)-1-(p-alkoxyphenyl)-2-nitroalkanes to provide highly effective synergistic compositions thereof.

The compounds preferred for use in this synergistic composition, along with the aforedefined methylenedioxyphenyl compounds have the following general structure:

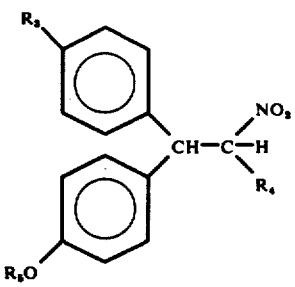

wherein $R_3$ is $C_4$ alkyl branched or unbranched, $R_4$ and $R_5$ are methyl ($CH_3$) or ethyl ($C_2H_5$). The preferred compound is where $R_4$ and $R_5$ are each ethyl, i.e., 1-(p-tertiary-butylphenyl)-1-(p-ethoxyphenyl)-2-nitrobutane.

Diphenyl compounds which contain alkyl and alkoxy, that is the 1-butylphenyl-1-methylenedioxyphenyl-2-nitroalkanes and the 1-butylphenyl-1-alkoxyphenyl-2-nitroalkanes, contain moities which are biodegradable and non-persistant in the environment. R. L. Metcalf et al. report in *Bull. Wld. Hlth. Org.*, 44, 363 (1971) that diphenyl compounds having alkyl and alkoxy substituent groups are readily attacked by multifunction oxidase enzymes present in the environment undergoing substantial biological degradation and do not appear to be readily stored or accumulated in animal tissues or other food chain. Unlike DDT, the compounds embodied herein, contain no chlorine, and are expected to be non-persistent and biodegradable in the environment, safe to mammals, bees and other non-target organisms. Additionally these compounds are broadly effective against a variety of insect pests.

Moreover these new compounds for example, 1-(4-butylphenyl)-1-(3,4-methylenedioxy)-2-nitroalkanes are highly effective synergists when used with other insecticides, for example, 1-(p-alkylphenyl)-1-(p-alkoxyphenyl)-2-nitroalkanes. That is, the degree of insect control achieved by the application of a mixture of compounds of the present invention with known insecticides is greater than one would expect from the additive contributions of the materials in the mixture. These compounds may be used singly in concentrations as low as 100 ppm or in combination at the low application rate of 25 ppm of active material.

DESCRIPTION OF PREFERRED EMBODIMENTS

Non-limiting examples of compounds according to this invention include: 1-(4-tert-butylphenyl)-1-(3,4-methylenedioxyphenyl)-2-nitrobutane and nitropropane; 1-(4-isobutylphenyl)-1-(3,4-methylenedioxyphenyl)-2-nitropropane and butane; 1-(4-sec-butylphenyl)-1-(3,4-methylenedioxyphenyl)-2-nitrobutane or propane, and 1-(4-n-butylphenyl)-1-(3,4-methylenedioxyphenyl)-2-nitrobutane or propane and the like.

In general, the compounds according to this invention are prepared by condensing 1,3-benzdioxole with 2-nitro-1-p-butylphenyl-1-alkanol in the presence of sulfuric acid. A solvent such as acetic acid, carbon tetrachloride, ethylene dichloride, methylene dichloride, or water may be employed or excess 1,3-benzdioxole may serve as solvent. The temperature of the reaction may vary from a $-10°$ C to a $+50°$ C.

Sulfuric acid and 1,3-benzdioxole are commercially available. The 2-nitro-1-p-butylphenyl-1-alkanols are prepared by condensing p-butylbenzaldehydes with 1-nitroethane and 1-nitropropane as illustrated below. The nitroalkanes are commercially available. The p-butylbenzaldehydes may be prepared according to the procedure of A. Rieche, H. Gross and E. Hoft, *Ber.* 93, 88 (1960) from commercially available butylbenzenes.

Examples 1 through 3 illustrate a convenient method for preparing said nitroalkanols. Examples 4 through 6 illustrate how the diphenylnitroalkanes according to this invention are generally prepared. The final products from the following described procedures (Examples 4–6) are mainly 1-(4-butylphenyl)-1-(3,4-methylenedioxyphenyl)-2-nitro-propanes and butanes but some 1-(4-butylphenyl)-1-(2,3-methylenedioxyphenyl)-2-nitropropanes and butanes and optical isomers may also be produced.

EXAMPLE 1

2-Nitro-1-(p-tert-butylphenyl)-1-butanol

A 81g. portion of p-tert-butylbenzaldehyde was added portion-wise over 0.5 hr. to a vigorously stirred solution of 57g. of sodium bisulfite in 500 ml of water and 200 ml of 95% ethanol. The resulting heterogeneous mixture was stirred overnight at ambient temperature. In a separate flask 89 g. of 1-nitropropane was added slowly at 5° C to a solution of 40 g of sodium hydroxide in 250 ml of 95% ethanol and 50 ml of water. The resulting yellow solution was stirred at ambient temperature for 0.5 hr. before it was added dropwise to the above heterogeneous mixture at 5° C with vigorous stirring. The resulting slurry was then stirred overnight at ambient temperature. The reaction mixture was filtered to remove a white solid precipitate, and the filtrate was diluted with 500 ml of water and extracted with 3 × 200ml of ethyl ether. The ethereal solution was washed with water and with saturated aqueous bicarbonate and then stirred with saturated sodium bisulfite until all unreacted benzaldehyde was removed as in insoluble bisulfite salt. The remaining ethereal solution was dried over magnesium sulfate and then concentrated under vacuum to remove solvent and unreacted 1-nitropropane. The residue which crystallized on trituration with hexane was recrystalized from hexane to afford 40g of product; mp 86°–88°; ir (KBr) 2.8 (s), 3.4 (s), 6.5 (s), 7.3 (s), 9.4 (m), 11.9 (s), 12.4 (m) microns; nmr ($CDCl_3$) 7.55 to 7.20 (4H), 4.7 to 4.4 (1H, m); 4.4 to 4.2 (1H, t), 3.0 (1H, broad), 1.95 (2H, m), 1.3 (9H, s), 0.8 (3H, m) ppm.

EXAMPLE 2

2-Nitro-1-(p-tert-butylphenyl)-1-propanol

The procedure of Example 1 was followed using 81g of p-tert-butylbenzaldehyde, 57g of sodium bisulfite, 75g of 1-nitroethane and 40g of sodium hydroxide with ethanol and water as solvents. The final product was recrystallized from hexane to provide 33g of white crystals: mp 86°–90°; ir (KBr) 2.8 (s), 3.5 (s), 6.4 (s), 7.35 (m), 9.8 (m), 11.9 (s) microns; nmr ($CDCl_3$) 7.45 to 7.15 (4H, m),5.0 to 4.6 (2H, m), 2.8 (1H, broad), 1.3 (6H, s), 1.4 to 1.2 (3H, d) ppm.

EXAMPLE 3

2-Nitro-1-(p-sec-butylphenyl)-1-butanol

A 1.0 ml portion of 3.7N potassium hydroxide in ethanol was added dropwise to a stirred, cooled (0°–5° C) solution of 9.7g of p-sec-butylbenzaldehyde and 16g of 1-nitropropane in 1.5 ml of ethanol. After two hours at 0°–5° C, one ml of glacial acetic acid was added and the organic products were extracted into ethyl ether (100 ml). The ethereal solution was washed with water, with saturated sodium bicarbonate and with brine and then stirred with a solution of 40g sodium bisulfite in 100 ml water and 30 ml methanol for overnight. The organic phase was dried over magnesium sulfate and evaporated to yield 13.6g of a viscous liquid. Trituration with 20/40 pet ether at $-10°$ C afforded 7.0g of a white solid: mp 59°–60° C; ir (KBr) 2.9 (s), 3.4 (s), 6.4 (s), 7.3 (m), 12.1 (m) microns; nmr ($CCl_4$) 7.09 (4H, s), 4.85 (1H, d of d), 4.4 (1H, sextet), 3.05 (1H, d), 2.60 (1H, m), 2.0 to 1.4 (4H, m), 1.19 (3H, d), 0.78 (6H, t) ppm.

EXAMPLE 4

1-(4-tert-Butylphenyl)-1-(3,4-methylenedioxyphenyl)-2-nitrobutane

A 5.0 ml portion of 96% sulfuric acid was added over 20 min to a cooled (5° to 15° C) solution of 10g of example 1 and 19.9g of 1,3-benzdioxole in 10 ml of methylene chloride. After another 1.0 hr, 30 ml of water was added slowly at 5° to 10° C and the organic products were extracted into ether. The ethereal solution was washed with water and with saturated bicarb, dried over magnesium sulfate and concentrated at 85° C (1.0 mm). The viscous residue (15 g) was mixed with 100 ml of 10% ether in hexane and set aside to cool and evaporate. The separated solid was collected, washed with hexane, air dried and recrystallized from 100 ml of methanol to afford 4.1g of a white powder: mp 135–7° C; ir (KBr) 3.4 (m), 6.4 (s), 6.7 (s), 8.0 (s), 8.2 (s), 9.7 (s), 12.8(m) microns; nmr (CDCl$_3$) 7.9 to 6.6 (7H, aromatic), 5.80 (2H, s), 5.10 (1H, dq), 4.27 (1H, d), 2.1 to 1.5 (2H, m), 1.22 (9H, s), 0.89 (3H, t) ppm.

EXAMPLE 5

1-(4-tert-Butylphenyl)-1-(3,4-methylenedioxyphenyl)-2-nitropropane

The procedure of Example 4 was followed for the reaction of 11.9g of Example 2 with 30g of 1,3-benzdioxole in 10 ml of methylene chloride and 5 ml of sulfuric acid. Obtained was 18.6g of a crude product which was crystallized and recrystallized from methanol to afford 5.5g of a white solid: mp 106°–114° C; ir (KBr) 3.4 (m), 6.4 (s), 6.7 (s), 6.8 (s), 8.1 (s), 9.6 (s), 10.8 (m), 12.4 (m) microns; nmr (CCl$_4$) 7.4 to 6.4 (7H, m), 5.79 (2H, s), 5.14 (1H, d of d), 4.16 (1H, d), 1.42 (3H, d), 1.21 (9H, s) ppm.

EXAMPLE 6

1-(4-sec-Butylphenyl)-1-(3,4-methylenedioxyphenyl)-2-nitrobutane

The procedure of Example 4 was followed for the reaction of 4.7g of Example 3 with 9.4g of 1,3-benzdioxole in 5 ml of dichloromethane and 2.5 ml of sulfuric acid. Obtained was 5.7g of a crude product which was filtered through 30g of silica gel with 1 l. of 30% dichloromethane in hexane and crystallized from 30/60 pet ether to afford 2.5 g of a white powder: mp 59°–63° C; ir (KBr) 3.4 (m), 6.4 (s), 6.7 (s), 6.8 (s), 8.0 (m), 8.2 (m), 9.7 (m) microns; nmr (CDCl$_3$) 7.03 (4H, s), 6.68 (1H, s), 6.63 (2H, q), 5.78 (2H, s), 4.98 (1H, dq), 4.18 (1H, d), 2.50 (1H, sextet), 2.0 to 1.35 (4H, m), 1.17 (3H, d), 0.88 (3H, t), 0.78 (3H, t) ppm.

EXAMPLE 7

The new 1-(4-butylphenyl)-1-(3,4-methylenedioxyphenyl)-2-nitroalkanes of this invention (Examples 4–6) were evaluated in standard greenhouse insecticide tests using housefly (HF), Mexican bean beetle (MB), Southern armyworm (SA) and yellow fever mosquito (YF). The rates of application were 500 and 100 ppm of active ingredient except in the mosquito test where test rates were 10 and 1 ppm. The results as set forth in Table I below indicate the percent kill of each insect species.

TEST METHODS

Housefly; 1 milliliter of an aqueous solution or suspension of the test compound was pipeted into a 9 cm. petri dish containing filter paper and 0.1 gram of granular sugar. Ten adult houseflies were admitted and the dish closed. Observations were made periodically for knockdown and at 24 hours for mortality. Mortality was primarily caused by stomach poisoning.

Southern armyworm and Mexican bean beetle; lima bean leaves of uniform size were momentarily dipped in a water-acetone solution of the test compound and the treated leaves were then placed on moistened filter paper in 9 cm. petri dishes and allowed to air dry. When dry, five, third or fourth instar larvae were introduced and encouraged to feed on the treated foliage by means of confinement. The dishes were closed and held for observation of mortality and feeding during a 48 to 72 hour period.

Yellow fever mosquito; fourth stage larvae were exposed to a solution of the active compound in water. The active material was initially dissolved in acetone and then added to the water. The compounds were screened at 10 ppm and at 1 ppm using approximately 10 larvae per 100 ml of treated water. Each treatment was replicated twice. Mortality was determined after 24 hour exposure.

TABLE I

| COMPOUND | RATE (ppm)* | HF | MB | SA | YF* |
|---|---|---|---|---|---|
| Example 4 | 500 | 100 | 100 | 100 | 100 |
|  | 100 | 20 | 100 | 100 | 40 |
| Example 5 | 500 | 100 | 100 | 100 | 100 |
|  | 100 | 10 | 100 | 80 | 100 |
| Example 6 | 500 | 100 | 100 | 100 | 100 |
|  | 100 | 100 | 90 | 30 | 100 |

*Application Rate = 500 and 100 ppm for HF, MB and SA,10 and 1 ppm for YF, i.e., 0.05, 0.01, 0.001 and 0.0001%by weight of the active material in each respective compositionwith a carrier.

In general, the 1-(p-alkylphenyl)-1-(p-alkoxyphenyl)-2-nitroalkanes for use in the synergistic compositions according to this invention are prepared by condensing ethoxybenzene (phenetole) with 2-nitro-1-p-C$_4$-alkylphenyl-1-alkanol in the presence of sulfuric acid. A solvent such as acetic acid, carbon tetrachloride, ethylene dichloride or water may be employed. Excess phenetole may also serve as solvent. The temperature of the reaction may vary from a −10° to a +50° C.

The starting materials (phenetole and sulfuric acid) are commercially available. The 2-nitro-1p-C$_4$-alkylphenyl-1-alkanols may be prepared by condensing p-alkylbenzaldehydes with 1-nitroethane or 1-nitropropane according to standard known procedures as illustrated above. The nitroalkanes are commercially available. The p-alkyl-benzaldehydes may be prepared according to the procedure of A. Reiche, H. Gross and E. Hoft, Ber., 93, 88 (1960) from commercially available alkylbenzenes.

Examples 1 through 3 illustrate a convenient method of preparing nitroalkanols useful in the preparation of the below described diphenyl alkanes for use in synergistic compositions (Examples 8 to 12) in accordance with the invention. Further, Example 13 illustrates the comparative insecticidal effectiveness of the synergistic compositions herein embodied; standard greenhouse insecticide evaluations described above were used.

EXAMPLE 8

1-(p-tert-Butylphenyl)-1-(p-ethoxyphenyl)-2-nitrobutane

To a 90 ml portion of 98% sulfuric acid were slowly added 33g of phenetole at 0° C. The solution was cooled to −15° C and a solution of 22.5g of Example 1 in 66g phenetole was added dropwise over one hour at −5° to −10° C. The reaction solution was stirred at −5° C for 1.5 hr. and then poured into 1 liter of ice and water. The organic products were extracted into ethyl ether, and the ethereal solution was washed with water, saturated bicarbonate and brine, dried over magnesium sulfate and concentrated. Excess phenetole was removed at the vacuum pump leaving a semi-solid residue weighing 24g. The residue was recrystallized twice from hexane to yield a purified sample: mp 95°–97°; ir (KBr) 3.4 (s), 6.7 (s), 7.3 (s), 8.0 (s), 9.6 (s), 12.2 (a) microns; nmr (CDCl$_3$) 7.3 to 7.0 and 6.9 to 6.6 (8H, m), 5.3 to 5.0 (1H, m), 4.2 (1H, d), 3,8 (2H, q), 1.7 (2H, broad), 1.2 (9H, s), 0.85 (3H, t) ppm; ms (molecular ion) 355.

EXAMPLE 9

1-(p-tert-Butylphenyl)-1-(p-ethoxyphenyl)-2-nitropropane

A 1.0 kg portion of 80% sulfuric acid was added dropwise to a solution of 237g of Example 2 in 732g of phenetole and the mixture was heated to 50° C for 2 hr. The acid layer was removed and the organic phase was diluted with ether. The ethereal solution was washed with water and with saturated sodium bicarbonate, dried over magnesium sulfate and evaporated. The crude residue which weighed 322g was triturated with 30/60 pet ether and recrystallized from isopropyl alcohol to afford a pure, white solid: mp 79°–82° C; ir (KBr) 3.4 (m), 6.5 (s), 6.6 (m), 8.0 (s), 9.5 (m), 12.2 (m) microns; nmr (CDCl$_3$) 7.4 to 6.7 (8H, m), 5.3 (1H, doublet of quartets), 4.3 (1H, d), 3.97 (2H, q), 1.45 (3H, d), 1.29 (3H, t), 1.22 (9H, s) ppm; ms (molecular ion) 341.

EXAMPLE 10

1-(p-sec-Butylphenyl)-1-(p-ethoxyphenyl)-2-nitrobutane

The procedure of Example 9 was followed for the reaction of 8.8g of Example 3 and 18.2g of phenetole with 25g of 80% sulfuric acid. Obtained were 11.7g of a yellow liquid which crystallized from 25 ml of 20/40 pet ether. The collected solid was recrystallized from methanol to afford 6.7g of white crystals: mp 89°–90° C; ir (KBr) 3.4 (m), 6.4 (a), 6.6 (s), 8.0 (s), 12.2 (m) microns; nmr (CCl$_4$) 7.2–6.5 (8H, m), 5.0 (1H, d of q), 4.21 (1H, d), 3.83 (2H, q), 2.48 (1H, sextet), 2.0 to 0.75 (16H, m) ppm.

EXAMPLE 11

The new 1-(4-butylphenyl)-1-(3,4-methylenedioxyphenyl)-2-nitroalkanes of this invention were evaluated as insecticide synergists in standard insecticide tests. In general the compounds of this invention were combined with the insecticide — 1-(p-tert-butylphenyl)-1-(p-ethoxyphenyl)-2-nitrobutane (pending application Serial No. 410,935, filed October 29, 1973) designated as Example 8 above — in varying proportions starting from, for example, 90% Example 4, 5 or 6 plus 10% Example 8 and decreasing to, for example 10% Example 4, 5 or 6, plus 90% Example 8. In all cases, the total sum of active ingredients (i.e. Examples 4, 5 or 6 plus 8) equaled 25 ppm. These mixtures were tested on housefly following the standard greenhouse test procedure, outlined above. The results as set forth below indicate the percent kill (or percent control) of the insect species:

TABLE II

| COMPOUND (% IN MIXTURE) | RATE* | % CONTROL |
| --- | --- | --- |
| Example 4 (100) | 25 ppm | 20% |
| Example 8 (100) | 25 ppm | 40% |
| Example 4 (10) + Example 8 (90) | 25 ppm | 80% |
| Example 4 (25) + Example 8 (75) | 25 ppm | 100% |
| Example 4 (50) + Example 8 (50) | 25 ppm | 100% |
| Example 4 (75) + Example 8 (25) | 25 ppm | 90% |
| Example 4 (90) + Example 8 (10) | 25 ppm | 20% |
| Example 6 (100) | 25 ppm | 0% |
| Example 8 (100) | 25 ppm | 40% |
| Example 6 (10) + Example 8 (90) | 25 ppm | 90% |
| Example 6 (25) + Example 8 (75) | 25 ppm | 90% |
| Example 6 (50) + Example 8 (50) | 25 ppm | 90% |
| Example 6 (75) + Example 8 (25) | 25 ppm | 50% |
| Example 6 (90) + Example 8 (10) | 25 ppm | 20% |

*Application Rate = 25 ppm (0.0025 wt. %) total of both active ingredients in composition with a carrier.

It is clear from the above described data that the effectiveness of the combinations is greater than one would predict from the sum of the effectiveness of the components.

The compounds embodied herein may be used in various ways to achieve effective insect control. They can be applied per se, as solids or in vaporized form, but are preferably applied as the toxic components in insect control compositions of a compound and an inert solid or liquid carrier. The compositions can also be applied as dusts, as liquid sprays, or as gas propelled sprays and can contain, in addition to a carrier, additives such as emulsifying agents, wetting agents, binding agents, gases compressed through the liquid state, odorants, stabilizers and the like. A wide variety of liquid and solid carriers can be used in the insect-control compositions. Non-limiting examples of liquid carriers, include water; organic solvents such as alcohols, ketones, amides and esters; mineral oils such as kerosene, light oils, medium oils; and vegetable oils such as cottonseed oil. Non-limiting examples of solid carriers include talc, bentonite, diatomaceous earth, pyrophyllite, fullers earth, gypsum, flours derived from cottonseeds and nutshells, and various natural and synthetic clays having a pH not exceeding about 9.5.

The amount of compounds of this invention utilized in insect-control compositions will vary rather widely. It depends to some extent upon the type of composition in which the material is being used, the nature of the condition to be controlled, and the method of application (i.e. spraying, dusting, etc.). In the ultimate insect-control composition as applied in the field, insect-control agent concentrations as low as 0.0001 weight percent of the total composition can be used. In general, compositions containing from about 0.01–0.05 weight percent insect-control agent in either liquid or solid carrier give excellent results. In some cases, however, stronger dosages of up to about 90 weight percent may be required.

The synergistic mixtures (that is the active material itself) may contain from 10–90 wt. % to 90–10 wt. % of each of the herein-embodied insect-control agents. That is a suitable composition thereof may comprise a mixture of insect-control agents having 10 wt. % of for example the compound of Example 4 and 90 wt. % of the compound of Example 8 (based on the total weight of the active material only) and vice versa and a suitable liquid or solid carrier. Compositions at the extremely low application rate of from about 0.001–0.005 weight percent of the active material in either liquid or solid carrier give excellent results. In some cases, dosages up to about 10 weight percent may be required. However, the synergistic compositions preferably containing about 0.0025 weight percent of both insect-control agents, for example about 12.5 ppm of each (25 ppm both) are highly effective. In practice, compositions for controlling insects utilizing these compounds are usually prepared in the form of concentrates which are diluted in the field to the concentration desired for application. For example, the concentrate can be a wettable powder containing large amounts of a compound according to this invention, a carrier (e.g., attapulgite or other clay), and wetting and dispersing agents. Such a powder can be diluted prior to application by dispersing it in water to obtain a sprayable suspension containing the concentration of insect-control agent desired for application. Other concentrates can be solutions that can be later diluted, e.g., with kerosene. Thus, it is within the contemplation of this invention to provide compositions combining superior insect activity with environmental safety. Such compositions may contain up to about 80%, by weight, of the composition of insecticidally-active compounds according to this invention. Accordingly, depending upon whether it is ready for application or it is in concentrated form the contemplated insect-control compositions may contain between about 0.0001 and about 80%, by weight of the composition, of an insecticidally-effective compound or synergistic mixture of compounds of this invention and a liquid or solid carrier as defined hereinabove.

Thus, the invention in addition to the new class of novel compounds described hereinabove also provides for a method of insect control comprising applying to the insect or its environment at least one compound or composition thereof or a composition comprising a synergistic mixture of compounds according to this invention in effective amounts to obtain said control.

Although the present invention has been described with preferred embodiments, it is to be understood that modifications and variations may be resorted to while not departing from the spirit and scope of this invention.

What is claimed is:

1. An insecticidally effective composition comprising about 0.001–0.005 weight percent, based on the total weight of the composition, of a synergistic combination of a compound having the structure:

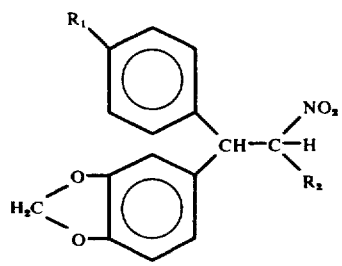

wherein $R_1$ is $C_4$ alkyl branched or unbranched and $R_2$ is methyl or ethyl and a compound having the structure:

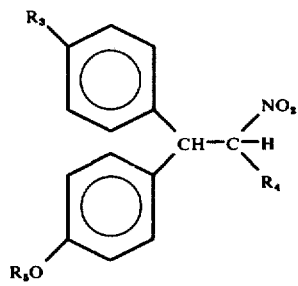

wherein $R_3$ is $C_4$ alkyl branched or unbranched, $R_4$ is methyl or ethyl and $R_5$ is ethyl, said synergistic combination containing 10–90 to 90–10 weight percent of each compound; and an inert solid or liquid carrier.

2. A composition according to claim 1 wherein $R_1$ and $R_3$ are both butyl.

3. A composition according to claim 1 wherein $R_1$ and $R_3$ are selected from the group consisting of normal butyl, secondary-butyl, isobutyl and tertiary-butyl.

4. A composition according to claim 1 where $R_1$ and $R_3$ are each tertiary-butyl and $R_2$, $R_4$ and $R_5$ are each ethyl.

5. A composition according to claim 1 wherein $R_1$ and $R_3$ are each tertiary-butyl, $R_2$ is methyl, and $R_4$ and $R_5$ are ethyl.

6. A method of insect-control comprising applying to an insect or its environment an insecticidally effective amount of a composition as described in claim 1.

7. The method of claim 6 wherein the active compounds contained in said composition are 1-(4-tertiary-butylphenyl)-1-(3,4-methylenedioxyphenyl)-2-nitrobutane and 1-(p-tertiary-butylphenyl)-1-(p-ethoxyphenyl)-2-nitrobutane.

8. The method of claim 6 wherein the active compounds contained in said composition are 1-(4-tertiary-butylphenyl-1-(3,4-methylenedioxyphenyl)-2-nitropropane and 1-(p-tertiary-butylphenyl)-1-(p-ethoxyphenyl)-2-nitrobutane.

9. The method of claim 6 wherein the active compounds contained in said composition are 1-(4-secondary-butylphenyl)-1-(3,4,methylenedioxyphenyl)-2-nitrobutane and 1-(p-tertiary-butylphenyl)-1-(p-ethoxyphenyl)-2-nitrobutane.

* * * * *

UNITED STATES PATENT AND TRADEMARK OFFICE
CERTIFICATE OF CORRECTION

PATENT NO. : 4,004,023

DATED : January 18, 1977

INVENTOR(S) : JERRY G. STRONG and HAROLD A. KAUFMAN

It is certified that error appears in the above-identified patent and that said Letters Patent are hereby corrected as shown below:

Column 1, line 13      " (3,4-methylenedioxyphenyl-2- " should be
--(3,4-methylenedioxyphenyl)-2- --

Column 6, line 40      " 2-nitro-1p-$C_4$ " should be
--2-nitro-1-p-$C_4$ --

Column 7, line 9      " 3,8 " should be -- 3.8 --

Column 9, line 34      " 0.0001 and about " should be
--0.0001% and about--

Signed and Sealed this twenty-third Day of August 1977

[SEAL]

Attest:

RUTH C. MASON
*Attesting Officer*

C. MARSHALL DANN
*Commissioner of Patents and Trademarks*